United States Patent [19]

Brownlee et al.

[11] 4,387,717
[45] Jun. 14, 1983

[54] PACER INTERNAL CARDIAC ELECTROGRAM SENSING SYSTEM

[75] Inventors: Robert R. Brownlee, State College; Howard C. Hughes, Jr., Cornwall; Paul H. Neff, Bellefonte, all of Pa.; G. Frank O. Tyers, Vancouver, Canada

[73] Assignee: Research Corporation, New York, N.Y.

[21] Appl. No.: 193,746

[22] Filed: Oct. 3, 1980

[51] Int. Cl.³ .............................................. A61N 1/36
[52] U.S. Cl. .............................. 128/419 PG; 128/786
[58] Field of Search ...... 128/419 P, 419 PG, 419 PT, 128/784, 785, 786

[56] References Cited

U.S. PATENT DOCUMENTS

| | | | |
|---|---|---|---|
| 3,478,476 | 11/1969 | Greatbatch | 128/419 PG |
| 3,648,707 | 3/1972 | Greatbatch | 128/419 PG |
| 3,893,461 | 8/1975 | Preston | 128/419 P |
| 3,920,024 | 11/1975 | Bowers | 128/419 P |
| 3,977,411 | 8/1976 | Hughes, Jr. et al. | 128/419 P |
| 4,091,817 | 5/1978 | Thaler | 128/419 PG |
| 4,166,470 | 9/1979 | Neumann | 128/419 PG |
| 4,289,134 | 9/1981 | Bernstein | 128/419 PG |

*Primary Examiner*—William E. Kamm
*Attorney, Agent, or Firm*—Cooper, Dunham, Clark, Griffin & Moran

[57] ABSTRACT

A system for internally sensing the cardiac electrogram in a patient with a cardiac pacemaker is disclosed comprising an implanted electrode that, in combination with the metallic case of the pacemaker which acts as an indifferent electrode, senses cardiac electrical signals and provides them as an input to the pacer electronics. The sensing electrode is appropriately spaced from the pacing electrode and positioned so that cross coupling is minimized to permit sensing of the cardiac electrogram without undue interference from the pacing stimulus and after potentials, and so that the pickup of both R- and P-waves is optimized. The sensed signals may be used to control atrial, ventricular or multichamber demand pacemakers and/or may be telemetered out of the patient for pickup and analysis by external equipment. A flat plate and a preferred cylindrical ring form of electrode are described.

10 Claims, 2 Drawing Figures

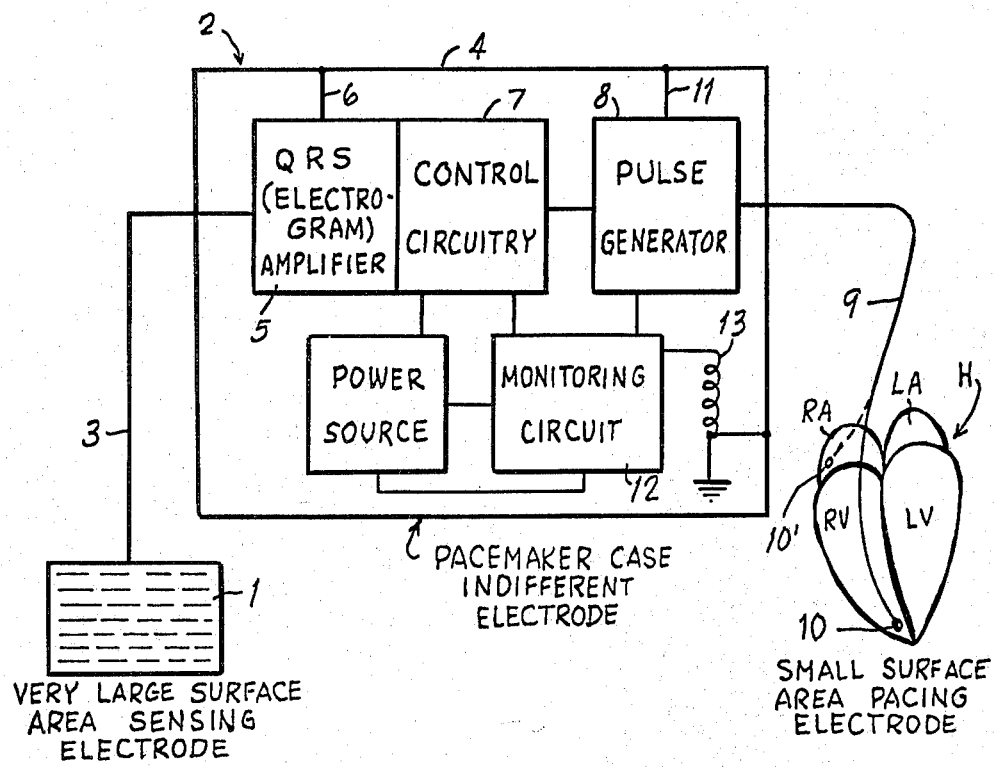
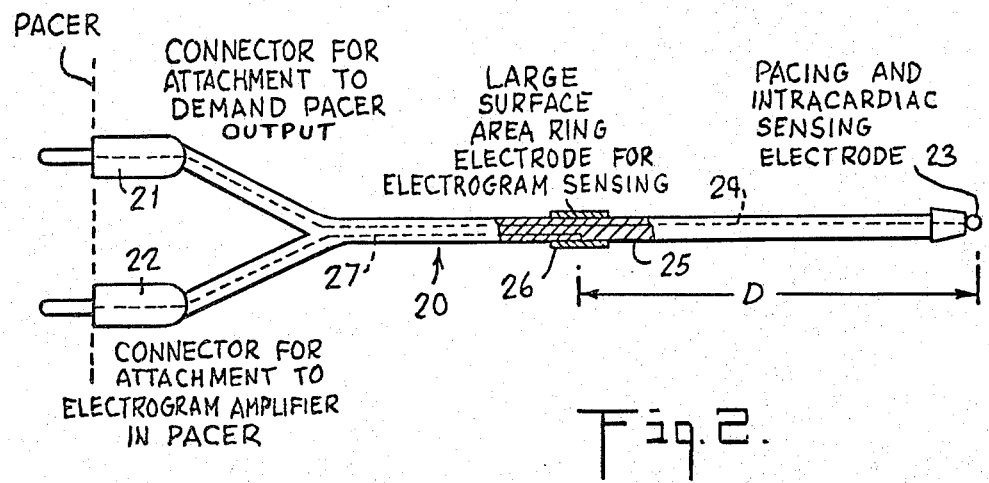

PACER INTERNAL CARDIAC ELECTROGRAM SENSING SYSTEM

BACKGROUND OF THE INVENTION

The present invention relates to the cardiac pacemaker art, and, more particularly, to a pacer electrode system with an implanted electrode for use in controlling a demand pacemaker and/or for monitoring the cardiac electrogram.

Presently, demand pacemakers are controlled by sensing the intracardiac electrogram, particularly the R-wave portion thereof, and using it to determine whether the pacemaker stimulus is required to sustain normal cardiac rate. The intracardiac electrogram is sensed by means of the same electrode, or electrode pair in a bipolar system, that is used for pacing the heart, and because intracardiac electrodes are either introduced into the heart through small veins or are sutured to te exterior wall of the heart, practical restrictions are placed on the size of the electrode. A problem is presented by this situation in that the electrode size affects both the pacing and sensing functions. For pacing, it is desirable to minimize the electrode surface area to achieve high current density, but, conversely, the size of the electrode should be maximized for optimal sensing of cardiac potentials. As a result, in the past, electrode design has frequently been a matter of compromising size to achieve a balance for both adequate pacing and sensing. An example of one solution for this problem is disclosed in U.S. Pat. No. 3,977,411.

However, in accordance with the present invention, it has now been determined that it is possible to overcome the size compromise problem and achieve improved sensing of cardiac potentials through the use of a separate electrode element, implanted near or in direct contact with the cardiac tissue, and positioned for sensing both R- and P-waves while avoiding interference from the pacing electrode. This separate element may be appropriately positioned with respect to the heart and the pacemaker casing, and have a comparatively large surface area, to optimize the electrical vector sensing of both R- and P-waves and to provide more stable sensing signals. The sensed signals may be fed to the pacer circuitry and used for improved atrial, ventricular or dual chamber demand pacemaker control or telemetered thereby to provide for the first time, noninvasive cardiac electrogram monitoring.

With telemetering from within the patient to an external analyzer for analysis, no skin or patient contact is required as in external cardiac electrogram monitoring. Consequently, currently-used EKG and rate dependent pacemaker follow-up techniques which require attachment of bracelets to the patient's extremities or pressure against the patient's wetted skin with three or four metal-footed conductive pickups are obviated along with their attendant disadvantages of time-consuming manipulation and artifact introduction.

SUMMARY OF THE INVENTION

The present invention involves an implantable electrode system that uses both an intracardiac pacing electrode, which is in direct contact with the cardiac tissue either by being placed transvenously in the right side of the heart or by being sutured to the cardiac muscle tissue, for stimulating the heart, and a separate sensing electrode, attached in the same manner or positioned in some remote location in the vascular system, for sensing cardiac electrical activity. The sensing electrode is carefully separated from the pacing electrode to minimize cross-coupling interference from the pacing pulses and after potentials, and is positioned to adequately sense both ventricular and atrial depolarization or R- and P-waves. This sensing is enhanced by selective positioning with respect to the atria and/or ventricles and relative to the pacemaker case which acts as an indifferent electrode. The relative positioning of the pacemaker case and the sensing electrode influences the magnitude and vector of the sensed signal so that this positioning may be used to optimize the signal level fed to the pacer circuitry.

The improved sensing electrode may be in the form of an extravascular large-surface-area metallic plate or preferably in the form of a cylindrical metal ring mounted on the insulated lead between the pacer and the pacing electrode, and the sensed signals may be used for controlling the pacer and/or telemetered for providing external monitoring of a patient's cardiac electrogram. Additionally, the electrogram or electrograms of the pacing electrode or electrodes may be monitored and telemetered to permit, for the first time, noninvasive determination of electrode displacement, which is currently the most common cause of early pacing system malfunctioning.

BRIEF DESCRIPTION OF THE DRAWINGS

FIG. 1 is a diagrammatic view of an electrode system in accordance with the present invention.

FIG. 2 is a view partly in section of a preferred form of electrode arrangement in accordance with the present invention.

DETAILED DESCRIPTION OF THE INVENTION

As shown in FIG. 1, the basic system of the present invention involves a separate sensing electrode, which may be in the form of a large-surface-area metallic plate 1 adapted for internal implantation in a patient, in combination with an implanted pacemaker 2, and a small surface area pacing electrode 10 which is inserted in or attached to the outer wall of the patient's heart H. As shown, the electrode 10 is inserted transvenously into the right ventricle of the heart H in contact with the right ventricular apex and receives pacing pulses from the pacer 2 over a suitable insulated lead 9. Another suitable insulated lead 3 is provided for conducting electrical signals between the sensing electrode 1 and the pacemaker 2 and supplies signals picked up by the plate 1 to a QRS amplifier 5 which is part of the circuitry within the pacer 2. It should be noted that as conventional QRS amplifiers also amplify P- and T-waves, they inherently act as cardiac electrogram amplifiers.

The amplifier 5 is provided with means 6 for grounding it to the pacer casing whereby the metallic case 4 may be made to act as an indifferent electrode in combination with the sensing electrode 1. The output of the amplifier 5 may be fed to the pacer control circuitry 7 for regulating the output of the pacemaker pulse generator 8. The pulse generator 8 output provides the cardiac stimulating pulses through insulated lead 9 to the pacing electrode 10. The pacemaker pulse generator 8 also has means 11 for grounding it to the pacemaker case 4.

The output of the amplifier 5 may also be fed through the control circuitry 7 to a monitoring circuit 12 whose output may be telemetered out of the patient by means of a coil 13 to an external sensing and analyzing system. Circuitry for these various purposes is known and within the purview of those skilled in the art. Through the use of an additional atrial stimulating electrode, such as electrode 10' in FIG. 1, improved demand control for so-called physiologic pacing, that is, atrial or atrioventricular sequential pacing, may also be provided, and atrial contact electrograms may be telemetered for external monitoring. Further, the pacing lead 9 may be used for transmitting ventricular contact electrograms for telemetering to confirm lead positioning, a good signal indicating proper positioning and a markedly reduced signal amplitude, as compared with that at implantation or immediately prior to testing, indicating improper positioning.

It will be appreciated that the separate sensing electrode 1 may be freely positioned within the patient without particular regard to the location of the pacing electrode 10, or additional electrodes as required for physiological pacing, except that electrode 1 should be spaced from the pacing electrodes to minimize cross coupling and interference from the pacing stimulus and after potentials. Since the position of the sensing electrode 1 with respect to the indifferent electrode formed by the pacemaker case 4 influences the magnitude and vector of the cardiac signal sensed, the relative positioning of these two electrodes may be adjusted until the sensed signal level is optimized. The optimized signal may then be used to provide improved control of the pacemaker system 2 as well as to facilitate external monitoring of the cardiac electrogram.

A particular preferred embodiment of the basic electrode system illustrated in FIG. 1, when the system is used for cardiac electrogram monitoring, is shown in FIG. 2. This preferred electrode system 20 is suitable for use with a ventricular demand pacemaker and is fitted with two connectors, a connector 21 for attachment to the output of the demand pacemaker electronics and a connector 22 for attachment to the input of a suitable amplifier contained within the pacemaker. The opposite end of the electrode system 20 is fitted at its tip with a pacing electrode 23 and has a separate sensing electrode 26. The system 20 may be constructed generally in the manner of that disclosed in U.S. Pat. No. 3,977,411 having an electrical lead 24, connected between the pacing electrode 23 and the connector 21 to the output of the pacemaker electronics, for passing pacing pulses to the heart and an electrical lead 27, connected between the sensing electrode 26 and the connector 22 for passing sensed signals to the pacer sensing electronics. An appropriate insulating sheath 25 is provided for the electrical leads 24 and 27.

In this preferred embodiment, the sensing electrode 26 is in the form of a cylindrical ring disposed on and about the insulating sheath 25 and capable of being positioned at a location spaced from the tip electrode 23, either within the heart itself, externally on the heart wall, or in some remote location in the vascular system away from the heart. It has been found that with selective positioning, not only the R-wave signal, which predominated among the signals sensed with the prior art sensing electrodes as they were coincident with or closely associated with the pacing electrode, but also an adequate P-wave signal, can be sensed by suitably locating the sensing electrode 26 with respect to the atria. Such positioning enhances the sensing of the cardiac electrogram and provides an improved signal which may ultimately be telemetered for external monitoring. The telemetered signal may readily be used to analyze and record the patient's cardiac electrogram, thus permitting the elimination of the need for any special external probes other than the telemetering pickup and obviating detection difficulties in thinner, older patients with uneven skin surfaces and metal-to-skin motion and other artifacts in the electrocardiogram introduced by such external skin contact probes.

Ring electrode 26 may also be disposed in an optimum relationship with the pacemaker casing 4 and the cardiac signal vector to achieve a maximum magnitude for the sensed signal, thus enhancing its use in controlling the demand pacemaker and in telemetering.

Electrode systems of this preferred type were tested by long term transvenous implantation in a number of mongrel dogs. It was found that as the position of the sensing electrode was successively displaced within the right ventricle farther from the right ventricular apex there were slight but insignificant decreases in the amplitude of the R-waves sensed. However, when the position of the sensing electrode was displaced through the tricuspid valve into the atrium there was a marked decrease in the amplitude of the R-waves sensed with an attendant significant increase in the amplitude of the P-waves sensed. It was accordingly appreciated that with a large surface area electrode direct contact with the myocardium is not required in order to achieve adequate detection of the P- and R-waves. Thus, it was demonstrated that by proper positioning of the large surface area electrode with respect to the heart in a system such as disclosed a patient's cardiac electrogram can be adequately detected for processing by conventional pacemaker circuitry.

It will accordingly be seen that an improved electrode system has been disclosed which permits improved control of multi- or single-chamber demand pacemakers and can be used to provide cardiac and peripheral internal electrogram signals for telemetering to an external analyzer for no-skin contact single-probe multiparameter telemetry and single (or potentially multiple) intracardiac and peripheral electrogram monitoring. In addition, the system may be used to optimize sensing position, either for atrial or ventricular pacemakers.

Use of the telemetering capability of the invention can significantly simplify pacemaker and electrocardiographic follow-up and transmission techniques, improve patient comfort, save physician, patient and monitoring service time, reduce telephone costs and improve the quality of the signal to be recorded or transmitted.

We claim:

1. A system, usable with a pacemaker containing heart-stimulating pacing circuitry including a QRS amplifier circuit, for sensing the cardiac electrical activity of a patient in whom the pacemaker is implanted to obtain an optimum cardiac electrogram signal and comprising:

casing means for housing said heart-stimulating pacing circuitry within the patient, at least a portion of the exterior of said casing means being electrically conditioned to act as an indifferent electrode;

pacing electrode means, implanted in the patient and operatively connected between said heart-stimulating pacing circuitry and the patient's heart, for conducting stimulating electrical pulses from said pacing circuitry to the heart; and a sensing electrode means, operatively connected to said indifferent electrode and to said QRS amplifier circuit of the pacing circitry and implanted in the patient at a selected position relative to the heart and said indifferent electrode and spaced from said pacing electrode means, for sensing cardiac electrical signal vectors with ventricular and atrial depolarization signals of comparable magnitude with respect to each other as in the patient's cardiac electrogram and conducting the sensed signals to said QRS amplifier circuit with minimized cross coupling of said stimulating electrical pulses and after potentials from said pacing electrode means.

2. A system as in claim 1 further comprising means in said heart-stimulating pacing circuitry for telemetering the sensed cardiac electrical signals out of the patient.

3. A system as in claim 1 wherein said pacing electrode means comprises:

a tip electrode in contact with the patient's heart;

first electrical lead means for conducting the stimulating pulses from the pacing circuitry to the tip electrode; and means for insulating said electrical lead means; and wherein said sensing electrode means comprises:

a ring electrode disposed about said insulating means; and second electrical lead means within said insulating means for conducting the sensed cardiac electrical signals to the pacing circuitry.

4. Apparatus as in claim 3 wherein said tip electrode and said ring electrode are disposed with respect to each other with said tip electrode in contact with the right ventricular apex of the heart, and said ring electrode out of contact with the right ventricular apex.

5. Apparatus as in claim 1 wherein said sensing electrode means comprises a large-area plate electrode.

6. A method of internally sensing the cardiac electrogram of a patient having an implanted pacemaker, including a casing with pacing circuitry therein, comprising the steps of:

disposing a pacing electrode, electrically connected to said pacemaker pacing circuitry, in contact with the patient's heart for applying stimulating electrical pulses from the pacemaker pacing circuitry to the heart;

forming at least a portion of the exterior of the pacemaker casing to act as an indifferent electrode; and disposing a sensing electrode, electrically connected to said pacemaker circuitry and said indifferent electrode, within the patient at a selected position with respect to said indifferent electrode and the heart and spaced from said pacing electrode, for sensing ventricular and atrial depolarization signals of comparable magnitude relative to each other as in the patient's cardiac electrogram and conducting the sensed signals to said pacemaker circuitry with minimized cross coupling of stimulating electrical pulses and after potentials from said pacing electrode.

7. The method of claim 6 comprising the further step of telemetering signals indicative of the ventricular and atrial depolarization signals sensed by said sensing electrode out of the patient for analysis.

8. The method of claim 6 wherein the pacing electrode is positioned in contact with the right ventricular apex of said heart and comprising the further steps of sensing the ventricular contact electrogram with said pacing electrode and telemetering signals indicative thereof out of the patient for analysis.

9. The method of claim 6 wherein the pacing electrode is positioned in contact with the right atrium of said heart and comprising the further steps of sensing the atrial contact electrogram with said pacing electrode and telemetering signals indicative thereof out of the patient for analysis.

10. The method of claim 6 wherein the pacing electrode is positioned in contact with the right ventricular apex of said heart and the sensing electrode is positioned in the right atrium of said heart.

* * * * *